United States Patent [19]

Herron et al.

[11] Patent Number: 5,137,537
[45] Date of Patent: Aug. 11, 1992

[54] ABSORBENT STRUCTURE CONTAINING INDIVIDUALIZED, POLYCARBOXYLIC ACID CROSSLINKED WOOD PULP CELLULOSE FIBERS

[75] Inventors: Carlisle M. Herron; David J. Cooper, both of Memphis, Tenn.

[73] Assignee: The Procter & Gamble Cellulose Company, Memphis, Tenn.

[21] Appl. No.: 596,607

[22] Filed: Oct. 17, 1990

Related U.S. Application Data

[63] Continuation-in-part of Ser. No. 432,705, Nov. 7, 1989, abandoned.

[51] Int. Cl.$^5$ ..................... D21H 11/20; D06M 13/00
[52] U.S. Cl. ........................................ 8/120; 8/116.1; 8/129; 8/115.62; 162/157.6
[58] Field of Search ................................ 8/120, 116.1

[56] References Cited

U.S. PATENT DOCUMENTS 2,759,787  8/1956  Touey et al. .............................. 8/120
3,526,048  9/1970  Rowland et al. ......................... 8/120

FOREIGN PATENT DOCUMENTS

0440472A1  8/1991  European Pat. Off. .

OTHER PUBLICATIONS

B. A. Kottes Andrews et al. "Efficient Ester Crosslink Finishing for Formaldehyde-Free Durable Press Cotton Fabrics" American Dyestuff Reporter, vol. 78, pp. 15-23 (Jun. 1989).

*Primary Examiner*—A. Lionel Clingman
*Attorney, Agent, or Firm*—Bart S. Hersko; Fredrick H. Braun; Richard C. Witte

[57] ABSTRACT

Disclosed are absorbent structures containing individualized, crosslinked fibers. The individualized, crosslinked fibers preferably have a $C_2$–$C_9$ polycarboxylic acid crosslinking agent reacted with the fibers in the form of intrafiber crosslink bonds. Preferably, the crosslinking agent is citric acid, and between about 0.5 mole % and about 10.0 mole % crosslinking agent react to form the intrafiber crosslink bonds. Also preferably, the absorbent structures have actual dry densities greater than their corresponding equilibrium wet densities, and expand upon wetting. The absorbent structures may also contain hydrogel-forming material.

27 Claims, No Drawings

ABSORBENT STRUCTURE CONTAINING INDIVIDUALIZED, POLYCARBOXYLIC ACID CROSSLINKED WOOD PULP CELLULOSE FIBERS

This application is a continuation-in-part of Ser. No. 07/432,705 filed Nov. 7, 1989 and since abandoned.

FIELD OF INVENTION

This invention is concerned with cellulosic fibers having high fluid absorption properties, and especially with absorbent structures made from such cellulosic fibers. More specifically, this invention is concerned with absorbent structures containing individualized, crosslinked, cellulosic fibers.

BACKGROUND OF THE INVENTION

Fibers crosslinked in substantially individualized form and various methods for making such fibers have been described in the art. The term "individualized, crosslinked fibers", refers to cellulosic fibers that have primarily intrafiber chemical crosslink bonds. That is, the crosslink bonds are primarily between cellulose molecules of a single fiber, rather than between cellulose molecules of separate fibers. Individualized, crosslinked fibers are generally regarded as being useful in absorbent product applications. The fibers themselves and absorbent structures containing individualized, crosslinked fibers generally exhibit an improvement in at least one significant absorbency property relative to conventional, uncrosslinked fibers. Often, the improvement in absorbency is reported in terms of absorbent capacity. Additionally, absorbent structures made from individualized crosslinked fibers generally exhibit increased wet resilience and increased dry resilience relative to absorbent structures made from uncrosslinked fibers. The term "resilience" shall hereinafter refer to the ability of pads made from cellulosic fibers to return toward an expanded original state upon release of a compressional force. Dry resilience specifically refers to the ability of an absorbent structure to expand upon release of compressional force applied while the fibers are in a substantially dry condition. Wet resilience specifically refers to the ability of an absorbent structure to expand upon release of compressional force applied while the fibers are in a moistened condition. For the purposes of this invention and consistency of disclosure, wet resilience shall be observed and reported for an absorbent structure moistened to saturation.

In general, three categories of processes have been reported for making individualized, crosslinked fibers. These processes, described below, are herein referred to as dry crosslinking processes, aqueous solution crosslinking processes, and substantially non-aqueous solution crosslinking processes.

Processes for making individualized, crosslinked fibers with dry crosslinking technology are described in U.S. Pat. No. 3,224,926, L. J. Bernardin, issued Dec. 21, 1965. Individualized, crosslinked fibers are produced by impregnating swollen fibers in an aqueous solution with crosslinking agent, dewatering and defiberizing the fibers by mechanical action, and drying the fibers at elevated temperature to effect crosslinking while the fibers are in a substantially individual state. The fibers are inherently crosslinked in an unswollen, collapsed state as a result of being dehydrated prior to crosslinking. Processes as exemplified in U.S. Pat. Nos. 3,224,926, wherein crosslinking is caused to occur while the fibers are in an unswollen, collapsed state, are referred to as processes for making "dry crosslinked" fibers. Dry crosslinked fibers are generally highly stiffened by crosslink bonds, and absorbent structures made therefrom exhibit relatively high wet and dry resilience. Dry crosslinked fibers are further characterized by low fluid retention values (FRV).

Processes for producing aqueous solution crosslinked fibers are disclosed, for example, in U.S. Pat. No. 3,241,553, F. H. Steiger, issued Mar. 22, 1966. Individualized, crosslinked fibers are produced by crosslinking the fibers in an aqueous solution containing a crosslinking agent and a catalyst. Fibers produced in this manner are hereinafter referred to as "aqueous solution crosslinked" fibers. Due to the swelling effect of water on cellulosic fibers, aqueous solution crosslinked fibers are crosslinked while in an uncollapsed, swollen state. Relative to dry crosslinked fibers, aqueous solution crosslinked fibers as disclosed in U.S. Pat. No. 3,241,553 have greater flexibility and less stiffness, and are characterized by higher fluid retention value (FRV). Absorbent structures made from aqueous solution crosslinked fibers exhibit lower wet and dry resilience than structures made from dry crosslinked fibers.

In U.S. Pat. No, 4,035,147, Sangenis et al., issued Jul. 12, 1977, a method is disclosed for producing individualized, crosslinked fibers by contacting dehydrated, nonswollen fibers with crosslinking agent and catalyst in a substantially nonaqueous solution which contains an insufficient amount of water to cause the fibers to swell. Crosslinking occurs while the fibers are in this substantially nonaqueous solution. This type of process shall hereinafter be referred to as a nonaqueous solution crosslinked process; and the fibers thereby produced shall be referred to as nonaqueous solution crosslinked fibers. The nonaqueous solution crosslinked fibers disclosed in U.S. Pat. No. 4,035,147 do not swell even upon extended contact with solutions known to those skilled in the art as swelling reagents. Like dry crosslinked fibers, they are highly stiffened by crosslink bonds, and absorbent structures made therefrom exhibit relatively high wet and dry resilience.

Crosslinked fibers as described above are believed to be useful for lower density absorbent product applications such as diapers and also higher density absorbent product applications such as catamenials. However, such fibers have not provided sufficient absorbency benefits, in view of their detriments and costs, over conventional fibers to result in significant commercial success. Commercial appeal of crosslinked fibers has also suffered due to safety concerns. The crosslinking agents most widely referred to in the literature are formaldehyde and formaldehyde addition products known as N-methylol agents or N-methylolamides, which, unfortunately, cause irritation to human skin and have been associated with other human safety concerns. Removal of free formaldehyde to sufficiently low levels in the crosslinked product such that irritation to skin and other human safety concerns are avoided has been hindered by both technical and economic barriers.

As mentioned above, the use of formaldehyde and various formaldehyde addition products to crosslink cellulosic fibers is known in the art. See, for example, U.S. Pat. No. 3,224,926, Bernardin, issued on Dec. 21, 1965; U.S. Pat. No. 3,241,553, Steiger, issued on Mar. 22, 1966; U.S. Pat. No. 3,932,209, Chatterjee, issued on Jan. 13, 1976; U.S. Pat. No. 4,035,147, Sangenis et al, issued on Jul. 12, 1977; and U.S. Pat. No. 3,756,913, Wodka, issued on Sep. 4, 1973. Unfortunately, the irritating effect of formaldehyde vapor on the eyes and skin is a marked disadvantage of such references. A need is evident for cellulosic fiber crosslinking agents that do not require formaldehyde or its unstable derivatives.

Other references disclose the use of dialdehyde crosslinking agents. See, for example, U.S. Pat. No. 4,689,118, Makoui et al, issued on Aug. 25, 1987; and U.S. Pat. No. 4,822,453, Dean et al, issued on Apr. 18, 1989. The Dean et al reference discloses absorbent structures containing individualized, crosslinked fibers, wherein the crosslinking agent is selected from the group consisting of $C_2$–$C_8$ dialdehydes, with glutaraldehyde being preferred. These references appear to overcome many of the disadvantages associated with formaldehyde and/or formaldehyde addition products. However, the cost associated with producing fibers crosslinked with dialdehyde crosslinking agents such as glutaraldehyde may be too high to result in significant commercial success. Therefore, there is a need to find cellulosic fiber crosslinking agents which are both safe for use on the human skin and also commercially feasible.

The use of polycarboxylic acids to impart wrinkle resistance to cotton fabrics is known in the art. See, for example, U.S. Pat. No. 3,526,048, Roland et al, issued Sep. 1, 1970; U.S. Pat. No. 2,971,815, Bullock et al, issued Feb. 14, 1961 and U.S. Pat. No. 4,820,307, Welch et al, issued Apr. 11, 1989. These references all pertain to treating cotton textile fabrics with polycarboxylic acids and specific curing catalysts to improve the wrinkle resistance and durability properties of the treated fabrics.

It has now been discovered that ester crosslinks can be imparted onto individualized cellulosic fibers through the use of specific polycarboxylic acid crosslinking agents. The ester crosslink bonds formed by the polycarboxylic acid crosslinking agents are different from the crosslink bonds that result from the mono- and di-aldehyde crosslinking agents, which form acetal crosslinked bonds. Applicants have found that absorbent structures made from these individualized, ester-crosslinked fibers exhibit increased wet resilience and dry resilience and improved responsiveness to wetting relative to structures containing uncrosslinked fibers. Importantly, the polycarboxylic acids disclosed for use in the present invention, are nontoxic, unlike formaldehyde and formaldehyde addition products commonly used in the art. Furthermore, the preferred polycarboxylic crosslinking agent i.e., citric acid, is available in large quantities at relatively low prices making it commercially competitive with the aldehyde crosslinking agents, without any of the related human safety concerns.

It is an object of this invention to provide individualized fibers crosslinked with a polycarboxylic acid crosslinking agent and absorbent structures made from such fibers wherein the absorbent structures made from the crosslinked fibers have higher levels of absorbent capacity relative to absorbent structures made from uncrosslinked fibers, and exhibit higher wet resilience and higher dry resilience than structures made from uncrosslinked fibers.

It is a further object of this invention to provide individualized fibers crosslinked with a polycarboxylic crosslinking agent and absorbent structures made from such fibers, as described above, which have a superior balance of absorbency properties relative to prior known crosslinked fibers.

It is additionally an object of this invention to provide commercially viable individualized, crosslinked fibers and absorbent structures made from such fibers, as described above, which can be safely utilized in the vicinity of human skin.

It is another object of this invention to provide absorbent structures having improved absorbent capacity and wicking which, in actual use, provide high levels of wearer skin dryness.

SUMMARY OF THE INVENTION

It has been found that the objects identified above may be met by individualized, crosslinked fibers and incorporation of these fibers into absorbent structures, as disclosed herein. Preferably, the individualized, crosslinked fibers having between about 0.5 mole % and about 10.0 mole %, more preferably between about 1.5 mole % and about 6.0 mole % crosslinking agent, calculated on a cellulose anhydroglucose molar basis, reacted with the fibers in the form of intrafiber crosslink bonds wherein the crosslinking agent is selected from the group consisting of $C_2$–$C_9$ polycarboxylic acids. The crosslinking agent is reacted with the fibers in an intrafiber crosslinking bond form. Such fibers, which are characterized by having water retention values (WRV's) of from about 25 to about 60, more preferably from about 28 to about 50, have been found to fulfill the identified objects relating to individualized, crosslinked fibers and provide unexpectedly good absorbent performance in absorbent structure applications.

The individualized, crosslinked fibers are, without limiting the scope of the invention, preferably formed into compressed absorbent structures that expand upon wetting.

The absorbent structures may additionally contain hydrogel-forming material. Significantly improved skin dryness and absorbent capacity and skin dryness of the wearer may be obtained with the utilization of hydrogel-forming material with individualized, crosslinked fibers. Significantly improved wicking and absorbent capacity are obtained by utilizing individualized, crosslinked fibers with hydrogel-forming material relative to utilizing conventional, uncrosslinked cellulose fibers with hydrogel-forming material. Surprisingly, such improved results may be obtained pursuant to the utilization of lower levels of hydrogel-forming material, calculated weight basis, for individualized, crosslinked fiber-containing pads compared to conventional cellulosic fiber pads.

DETAILED DESCRIPTION OF THE INVENTION

Cellulosic fibers of diverse natural origin are applicable to the invention. Digested fibers from softwood, hardwood or cotton linters are preferably utilized. Fibers from Esparto grass, bagasse, kemp, flax, and other lignaceous and cellulosic fiber sources may also be utilized as raw material in the invention. The fibers may be supplied in slurry, unsheeted or sheeted form. Fibers supplied as wet lap, dry lap or other sheeted form are preferably rendered into unsheeted form by mechanically disintegrating the sheet, preferably prior to contacting the fibers with the crosslinking agent. Also, preferably the fibers are provided in a wet or moistened condition. Most preferably, the fibers are never-dried fibers. In the case of dry lap, it is advantageous to moisten the fibers prior to mechanical disintegration in order to minimize damage to the fibers.

The optimum fiber source utilized in conjunction with this invention will depend upon the particular end use contemplated. Generally, pulp fibers made by chemical pulping processes are preferred. Completely bleached, partially bleached and unbleached fibers are applicable. It may frequently be desired to utilize bleached pulp for its superior brightness and consumer appeal. For products such as paper towels and absorbent pads for diapers, sanitary napkins, catamenials, and other similar absorbent paper products, it is especially preferred to utilize fibers from southern softwood pulp due to their premium absorbency characteristics.

Crosslinking agents applicable to the present development include aliphatic and alicyclic $C_2-C_9$ polycarboxylic acids. As used herein, the term "$C_2-C_9$ polycarboxylic acid" refers to an organic acid containing two or more carboxyl (COOH) groups and from 2 to 9 carbon atoms in the chain or ring to which the carboxyl groups are attached. The carboxyl groups are not included when determining the number of carbon atoms in the chain or ring. For example, 1,2,3 propane tricarboxylic acid would be considered to be a $C_3$ polycarboxylic acid containing three carboxyl groups. Similarly, 1,2,3,4 butane tetracarboxylic acid would be considered to be a $C_4$ polycarboxylic acid containing four carboxyl groups.

More specifically, the $C_2-C_9$ polycarboxylic acids suitable for use as cellulose crosslinking agents in the present invention include aliphatic and alicyclic acids either olefinically saturated or unsaturated with at least three and preferably more carboxyl groups per molecule or with two carboxyl groups per molecule if a carbon-carbon double bond is present alpha, beta to one or both carboxyl groups. An additional requirement is that to be reactive in esterifying cellulose hydroxyl groups, a given carboxyl group in an aliphatic or alicyclic polycarboxylic acid must be separated from a second carboxyl group by no less than 2 carbon atoms and no more than three carbon atoms. Without being bound by theory, it appears from these requirements that for a carboxyl group to be reactive, it must be able to form a cyclic 5- or 6-membered anhydride ring with a neighboring carboxyl group in the polycarboxylic acid molecule. Where two carboxyl groups are separated by a carbon-carbon double bond or are both connected to the same ring, the two carboxyl groups must be in the cis configuration relative to each other if they are to interact in this manner.

In aliphatic polycarboxylic acids containing three or more carboxyl groups per molecule, a hydroxyl group attached to a carbon atom alpha to a carboxyl group does not interfere with the esterification and crosslinking of the cellulosic fibers by the acid. Thus, polycarboxylic acids such as citric acid (also known as 2-hydroxy-1,2,3 propane tricarboxylic acid) and tartrate monosuccinic acids are suitable as crosslinking agents in the present development.

The aliphatic or alicyclic $C_2-C_9$ polycarboxylic acid crosslinking agents may also contain an oxygen or sulfur atom(s) in the chain or ring to which the carboxyl groups are attached. Thus, polycarboxylic acids such as oxydisuccinic acid also known as 2,2'-oxybis(butanedioic acid), thiodisuccinic acid, and the like, are meant to be included within the scope of the invention. For purposes of the present invention, oxydisuccinic acid would be considered to be a $C_4$ polycarboxylic acid containing four carboxyl groups.

Examples of specific polycarboxylic acids which fall within the scope of this invention include the following: maleic acid, citraconic acid also known as methylmaleic acid, citric acid, itaconic acid also known as methylenesuccinic acid, tricarballylic acid also known as 1,2,3 propane tricarboxylic acid, transaconitic acid also known as trans-1-propene-1,2,3-tricarboxylic acid, 1,2,3,4-butanetetracarboxylic acid, all-cis-1,2,3,4-cyclopentanetetracarboxylic acid, mellitic acid also known as benzenehexacarboxylic acid, and oxydisuccinic acid also known as 2,2'-oxybis(butanedioic acid). The above list of specific polycarboxylic acids is for exemplary purposes only, and is not intended to be all inclusive. Importantly, the crosslinking agent must be capable of reacting with at least two hydroxyl groups on proximately located cellulose chains in a single cellulosic fiber.

Preferably, the $C_2-C_9$ polycarboxylic acids used herein are aliphatic, saturated, and contain at least three carboxyl groups per molecule. One group of preferred polycarboxylic acid crosslinking agents for use with the present invention include citric acid also known as 2-hydroxy-1,2,3 propane tricarboxylic acid, 1,2,3 propane tricarboxylic acid, and 1,2,3,4 butane tetracarboxylic acid. Citric acid is especially preferred, since it has provided fibers with high levels of absorbency and resiliency, is safe and non-irritating to human skin, and has provided stable, crosslink bonds. Furthermore, citric acid is available in large quantities at relatively low prices, thereby making it commercially feasible for use as a crosslinking agent.

Another group of preferred crosslinking agents for use in the present invention includes saturated $C_2-C_9$ polycarboxylic acids containing at least one oxygen atom in the chain to which the carboxyl groups are attached. Examples of such compounds include oxydisuccinic acid, tartrate monosuccinic acid having the structural formula:

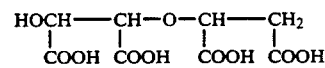

and tartrate disuccinic acid having the structural formula:

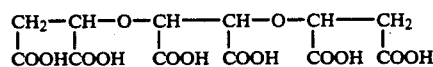

A more detailed description of tartrate monosuccinic acid, tartrate disuccinic acid, and salts thereof, can be found in U.S. Pat. No. 4,663,071, Bush et al., issued May 5, 1987, incorporated herein by reference.

Those knowledgeable in the area of polycarboxylic acids will recognize that the aliphatic and alicyclic $C_2-C_9$ polycarboxylic acid crosslinking agents described above may be present in a variety of forms, such as the free acid form, and salts thereof. Although the free acid form is preferred, all such forms are meant to be included within the scope of the invention.

The individualized, crosslinked fibers used in the absorbent structures of the present invention have an effective amount of the $C_2-C_9$ polycarboxylic acid crosslinking agent reacted with the fibers in the form of intrafiber crosslink bonds. As used herein, "effective amount of crosslinking agent" refers to an amount of crosslinking agent sufficient to provide an improvement in at least one significant absorbency property of the fibers themselves and/or absorbent structures containing the individualized, crosslinked fibers, relative to conventional, uncrosslinked fibers. One example of a significant absorbency property is drip capacity, which is a combined measurement of an absorbent structure's fluid absorbent capacity and fluid absorbency rate. A detailed description of the procedure for determining drip capacity is provided hereinafter.

In particular, unexpectedly good results are obtained for absorbent pads made from individualized, crosslinked fibers having between about 0.5 mole % and about 10.0 mole %, more preferably between about 1.5 mole % and about 6.0 mole % crosslinking agent, calculated on a cellulose anhydroglucose molar basis, reacted with the fibers.

Preferably, the crosslinking agent is contacted with the fibers in a liquid medium, under such conditions that the crosslinking agent penetrates into the interior of the individual fiber structures. However, other methods of crosslinking agent treatment, including spraying of the fibers while in individualized, fluffed form, are also within the scope of the invention.

Applicants have discovered that the crosslinking reaction can be accomplished at practical rates without a catalyst, provided the pH is kept within a particular range (to be discussed in more detail below). This is contrary to the prior art which teaches that specific catalysts are needed to provide sufficiently rapid esterification and crosslinking of fibrous cellulose by polycarboxylic acid crosslinking agents to be commercially feasible. See, for example, U.S. Pat. No. 4,820,307, Welch et al., issued Apr. 11, 1989.

However, if desired, the fibers can also be contacted with an appropriate catalyst prior to crosslinking. Applicants have found that the type, amount, and method of contact of catalyst to the fibers will be dependent upon the particular crosslinking process practiced. These variables will be discussed in more detail below.

Once the fibers are treated with crosslinking agent (and catalyst if one is used), the crosslinking agent is caused to react with the fibers in the substantial absence of interfiber bonds, i.e., while interfiber contact is maintained at a low degree of occurrence relative to unfluffed pulp fibers, or the fibers are submerged in a solution that does not facilitate the formation of interfiber bonding, especially hydrogen bonding. This results in the formation of crosslink bonds which are intrafiber in nature. Under these conditions, the crosslinking agent reacts to form crosslink bonds between hydroxyl groups of a single cellulose chain or between hydroxyl groups of proximately located cellulose chains of a single cellulosic fiber.

Although not presented or intended to limit the scope of the invention, it is believed that the carboxyl groups on the polycarboxylic acid crosslinking agent react with the hydroxyl groups of the cellulose to form ester bonds. The formation of ester bonds, believed to be the desirable bond type providing stable crosslink bonds, is favored under acidic reaction conditions. Therefore, acidic crosslinking conditions, i.e. pH ranges of from about 1.5 to about 5, are highly preferred for the purposes of this invention.

The fibers are preferably mechanically defibrated into a low density, individualized, fibrous form known as "fluff" prior to reaction of the crosslinking agent with the fibers. Mechanical defibration may be performed by a variety of methods which are presently known in the art or which may hereafter become known. Mechanical defibration is preferably performed by a method wherein knot formation and fiber damage are minimized. One type of device which has been found to be particularly useful for defibrating the cellulosic fibers is the three stage fluffing device described in U.S. Pat. No. 3,987,968, issued to D. R. Moore and O. A. Shields on Oct. 26, 1976, said patent being hereby expressly incorporated by reference into this disclosure. The fluffing device described in U.S. Pat. No. 3,987,968 subjects moist cellulosic pulp fibers to a combination of mechanical impact, mechanical agitation, air agitation and a limited amount of air drying to create a substantially knot-free fluff. The individualized fibers have imparted thereto an enhanced degree of curl and twist relative to the amount of curl and twist naturally present in such fibers. It is believed that this additional curl and twist enhances the resilient character of absorbent structures made from the finished, crosslinked fibers.

Other applicable methods for defibrating the cellulosic fibers include, but are not limited to, treatment with a Waring blender and tangentially contacting the fibers with a rotating disk refiner or wire brush. Preferably, an air stream is directed toward the fibers during such defibration to aid in separating the fibers into substantially individual form.

Regardless of the particular mechanical device used to form the fluff, the fibers are preferably mechanically treated while initially containing at least about 20% moisture, and preferably containing between about 40% and about 65% moisture.

Mechanical refining of fibers at high consistency or of partially dried fibers may also be utilized to provide curl or twist to the fibers in addition to curl or twist imparted as a result of mechanical defibration.

The fibers made according to the present invention have unique combinations of stiffness and resiliency, which allow absorbent structures made from the fibers to maintain high levels of absorptivity, and exhibit high levels of resiliency and an expansionary responsiveness to wetting of a dry, compressed absorbent structure. In addition to having the levels of crosslinking within the stated ranges, the crosslinked fibers are characterized by having water retention values (WRV's) of less than about 60, preferably from about 28 to about 50, and more preferably between about 30 and about 45, for conventional, chemically pulped, papermaking fibers. The WRV of a particular fiber is indicative of the level .of crosslinking. Very highly crosslinked fibers, such as those produced by many of the prior art known crosslinking processes previously discussed, have been found to have WRV's of less than about 25, and generally less than about 20. The particular crosslinking process utilized will, of course, affect the WRV of the crosslinked fiber. However, any process which will result in crosslinking levels and WRV's within the stated limits is believed to be, and is intended to be, within the scope of this invention. Applicable methods of crosslinking include dry crosslinking processes and nonaqueous solution crosslinking processes as generally discussed in the Background Of The Invention. Certain preferred dry crosslinking and nonaqueous solution crosslinking processes for preparing the individualized, crosslinked fibers of the present invention, will be discussed in more detail below. Aqueous solution crosslinking processes wherein the solution causes the fibers to become highly swollen will result in fibers having WRV's which are in excess of about 60. These fibers will provide insufficient stiffness and resiliency for the purposes of the present invention.

Specifically referring to dry crosslinking processes, individualized, crosslinked fibers may be produced from such a process by providing a quantity of cellulosic fibers, contacting a slurry of the fibers with a type and amount of crosslinking agent as described above, mechanically separating, e.g., defibrating, the fibers into substantially individual form, and drying the fibers and causing the crosslinking agent to react with the fibers in the presence of a catalyst to form crosslink bonds while the fibers are maintained in substantially individual form. The defibration step, apart from the drying step, is believed to impart additional curl. Subsequent drying is accompanied by twisting of the fibers, with the degree of twist being enhanced by the curled geometry of the fiber. As used herein, fiber "curl" refers to a geometric curvature of the fiber about the longitudinal axis of the fiber. "Twist" refers to a rotation of the fiber about the perpendicular cross-section of the longitudinal axis of the fiber. The fibers of the preferred embodiment of the present invention are individualized, crosslinked in intrafiber bond form, and are highly twisted and curled.

As used herein, the term "twist count" refers to the number of twist nodes present in a certain length of fiber. Twist count is utilized as a means of measuring the degree to which a fiber is rotated about its longitudinal axis. The term "twist node" refers to a substantially axial rotation of 180° about the longitudinal axis of the fiber, wherein a portion of the fiber (i.e., the "node") appears dark relative to the rest of the fiber when viewed under a microscope with transmitted light. The distance between nodes corresponds to an axial rotation of 180°. Those skilled in the art will recognize that the occurrence of a twist node as described above, is primarily a visual rather than a physical phenomena. However, the number of twist nodes in a certain length of fibers (i.e., the twist count) is directly indicative of the degree of fiber twist, which is a physical parameter of the fiber. The appearance and quantity of twist nodes will vary depending upon whether the fiber is a summerwood fiber or a springwood fiber. The twist nodes and total twist count are determined by a Twist Count Image Analysis Method which is described in the Experimental Method section of the disclosure. The average twist count referred to in describing the fibers of the present invention is properly determined by the aforementioned twist count method. When counting twist nodes, portions of fiber darkened due to fiber damage or fiber compression should be distinguished from portions of fiber appearing darkened due to fiber twisting.

The actual twist count of any given sample of fibers will vary depending upon the ratio of springwood fibers to summerwood fibers. The twist count of any particular springwood or summerwood fibers will also vary from fiber to fiber. Notwithstanding the above, the average twist count limitations are useful in defining the invention, and these limitations apply regardless of the particular combination of springwood fibers and summerwood fibers. That is, any mass of fibers having twist count encompassed by the stated twist count limitations are meant to be encompassed within the scope of the present invention, so long as the other claimed limitations are met.

In the measurement of twist count for a sample of fibers, it is important that a sufficient amount of fibers be examined in order to accurately represent the average level of twist of the variable individual fiber twist levels. It is suggested that at least five (5) inches of cumulative fiber length of a representative sample of a mass of fibers be tested in order to provide a representative fiber twist count.

The wet fiber twist count is described and measured analogously to the dry fiber twist count, said method varying only in that the fiber is wetted with water prior to being treated and the twist nodes are then counted while wet in accordance with the Twist Count Image Analysis Method.

Preferably, the average dry fiber twist count is at least about 2.5 twist nodes per millimeter, and the average wet fiber twist count is at least about 1.5 twist nodes per millimeter and is at least 1.0 twist nodes per millimeter less than its dry fiber twist count. Most preferably, the average dry fiber twist count is at least about 3.0 twist nodes per millimeter, and the average wet fiber twist count is at least about 2.0 twist nodes per millimeter and is at least 1.0 twist nodes per millimeter less than the dry fiber twist count.

In addition to being twisted, the fibers of the present invention are curled. Fiber curl may be described as a fractional shortening of the fiber due to kinks, twists, and/or bends in the fiber. For the purposes of this disclosure, fiber curl shall be measured in terms of a two dimensional field. The level of fiber curl shall be referred to in terms of a fiber curl index. The fiber curl factor, a two dimensional measurement of curl, is determined by viewing the fiber in a two dimensional plane, measuring the projected length of the fiber as the longest dimension of a rectangle encompassing the fiber, $L_R$, and the actual length of the fiber $L_A$, and then calculating the fiber curl factor from the following equation:

$$Curl\ Factor = (L_A/L_R) - 1 \tag{1}$$

A Fiber Curl Index Image Analysis Method is utilized to measure $L_R$ and $L_A$. This method is described in the Experimental Methods section of this disclosure. The background information for this method is described in the 1979 International Paper Physics Conference Symposium, The Harrison Hotel, Harrison Hot Springs, British Columbia, Sep. 17–19, 1979 in a paper titled "Application Of Image Analysis To Pulp Fibre Characterization: Part 1," by B. D. Jordan and D. H. Page, pp. 104–114, Canadian Pulp and Paper Association (Montreal, Quebec, Canada), said reference being incorporated by reference into this disclosure.

Preferably, the fibers have a curl factor of at least about 0.30, and more preferably of at least about 0.50.

Maintaining the fibers in substantially individual form during drying and crosslinking allows the fibers to twist during drying and thereby be crosslinked in such twisted, curled state. Drying fibers under such conditions that the fibers may twist and curl is referred to as drying the fibers under substantially unrestrained conditions. On the other hand, drying fibers in sheeted form results in dried fibers which are not as highly twisted and curled as fibers dried in substantially individualized form. It is believed that interfiber hydrogen bonding "restrains" the relative occurrence of twisting and curling of the fiber.

There are various methods by which the fibers may be contacted with the crosslinking agent and catalyst (if a catalyst is used). In one embodiment, the fibers are contacted with a solution which initially contains both the crosslinking agent and the catalyst. In another embodiment, the fibers are contacted with an aqueous solution of crosslinking agent and allowed to soak prior to addition of the catalyst. The catalyst is subsequently added. In a third embodiment, the crosslinking agent and catalyst are added to an aqueous slurry of the cellulosic fibers. Other methods in addition to those described herein will be apparent to those skilled in the art, and are intended to be included within the scope of this invention. Regardless of the particular method by which the fibers are contacted with crosslinking agent and catalyst (if a catalyst is used), the cellulosic fibers, crosslinking agent and catalyst are preferably mixed and/or allowed to soak sufficiently with the fibers to assure thorough contact with and impregnation of the individual fibers.

Applicants have discovered that the crosslinking reaction can be accomplished without the use of a catalyst if the pH of the solution containing the crosslinking agent is kept within the ranges specified hereinafter. In particular, the aqueous portion of the cellulosic fiber slurry or crosslinking agent solution should be adjusted to a target pH of between about pH 1.5 and about pH 5, more preferably between about pH 2.0 and about pH 3.5, during the period of contact between the crosslinking agent and the fibers. Preferably, the pH is adjusted by the addition of a base, such as sodium hydroxide, to the crosslinking agent solution.

Notwithstanding the above, in general, any substance which can catalyze the crosslinking mechanism may be utilized. Applicable catalysts include alkali metal hypophosphites, alkali metal phosphites, alkali metal polyphosphates, alkali metal phosphates, and alkali metal sulfates. Especially preferred catalysts are the alkali metal hypophosphites, alkali metal phosphates, and alkali metal sulfates. The mechanism of the catalysis is unknown, although applicants believe that the catalysts may simply be functioning as buffering agents, keeping the pH levels within the desired ranges. A more complete list of catalysts useful herein can be found in U.S. Pat. No. 4,820,307, Welch et al, issued April 1989, incorporated herein by reference. The selected catalyst may be utilized as the sole catalyzing agent, or in combination with one or more other catalysts.

The amount of catalyst preferably utilized is, of course, dependent upon the particular type and amount of crosslinking agent and the reaction conditions, especially temperature and pH. In general, based upon technical and economic considerations, catalyst levels of between about 5 wt. % and about 80 wt. %, based on the weight of crosslinking agent added to the cellulosic fibers, are preferred. For exemplary purposes, in the case wherein the catalyst utilized is sodium hypophosphite and the crosslinking agent is citric acid, a catalyst level of about 50 wt. %, based upon the amount of citric acid added, is preferred. It is additionally desirable to adjust the aqueous portion of the cellulosic fiber slurry or crosslinking agent solution to a target pH of between about pH 1.5 and about pH 5, more preferably between about pH 2.0 and about pH 3.5, during the period of contact between the crosslinking agent and the fibers.

The cellulosic fibers should generally be dewatered and optionally dried. The workable and optimal consistencies will vary depending upon the type of fluffing equipment utilized. In the preferred embodiments, the cellulosic fibers are dewatered and optimally dried to a consistency of between about 20% and about 80%. More preferably, the fibers are dewatered and dried to a consistency level of between about 35% and about 60%. Drying the fibers to within these preferred ranges generally will facilitate defibration of the fibers into individualized form without excessive formation of knots associated with higher moisture levels and without high levels of fiber damage associated with lower moisture levels.

For exemplary purposes, dewatering may be accomplished by such methods as mechanically pressing, centrifuging, or air drying the pulp. Additional drying of the fibers within the 35-60% consistency range previously described is optional but is preferably performed by a method, known in the art as air drying, under conditions such that the utilization of high temperature for an extended period of time is not required. Excessively high temperature and time in this stage may result in drying the fibers beyond 60% consistency, thereby possibly producing excessive fiber damage during the ensuing defibration stage. After dewatering, the fibers are then mechanically defibrated as previously described.

The defibrated fibers are then dried to between 60% and 100% consistency by a method known in the art as flash drying. This stage imparts additional twist and curl to the fibers as water is removed from them. While the amount of water removed by this additional drying step may be varied, it is believed that flash drying to higher consistency provides a greater level of fiber twist and curl than does flash drying to a consistency in the lower part of the 60%-100% range. In the preferred embodiments, the fibers are dried to about 90%-95% consistency. It is believed that this level of flash drying provides the desired level of fiber twist and curl without requiring the higher flash drying temperatures and retention times required to reach 100% consistency. Flash drying the fibers to a consistency, such as 90%-95%, in the higher portion of the 60%-100% range also reduces the amount of drying which must be accomplished in the curing stage following flash drying.

The flash dried fibers are then heated to a suitable temperature for an effective period of time to cause the crosslinking agent to cure, i.e., to react with the cellulosic fibers. The rate and degree of crosslinking depends upon dryness of the fiber, temperature, pH, amount and type of catalyst and crosslinking agent and the method utilized for heating and/or drying the fibers while crosslinking is performed. Crosslinking at a particular temperature will occur at a higher rate for fibers of a certain initial moisture content when accompanied by a continuous, air-through drying than when subjected to drying/heating in a static oven. Those skilled in the art will recognize that a number of temperature-time relationships exist for the curing of the crosslinking agent. Drying temperatures from about 145° C. to about 165° C. for periods of between about 30 minutes and 60 minutes, under static, atmospheric conditions will generally provide acceptable curing efficiencies for fibers having moisture contents less than about 10%. Those skilled in the art will also appreciate that higher temperatures and forced air convection decrease the time required for curing. Thus, drying temperatures from about 170° C. to about 190° C. for periods of between about 2 minutes and 20 minutes, in an air-through oven will also generally provide acceptable curing efficiencies for fibers having moisture contents less than about 10%. Curing temperatures should be maintained at less than about 225° C., preferably less than about 200° C., since exposure of the fibers to such high temperatures may lead to darkening or other damaging of the fibers.

Without being bound by theory, it is believed that the chemical reaction of the cellulosic fibers with the $C_2$–$C_9$ polycarboxylic acid crosslinking agent does not begin until the mixture of these materials is heated in the curing oven. During the cure stage, ester crosslink bonds are formed between the $C_2$–$C_9$ polycarboxylic acid crosslinking agent and the cellulose molecules. These ester crosslinkages are mobile under the influence of heat, due to a transesterification reaction which takes place between ester groups and adjacent unesterified hydroxyl groups on the cellulosic fibers. It is further believed that the process of transesterification, which occurs after the initial ester bonds are formed, results in fibers which have improved absorbency properties compared to fibers that are not cured sufficiently to allow transesterification to occur.

Following the crosslinking step, the fibers are washed, if desired. After washing, the fibers are defluidized and dried. The fibers while still in a moist condition may be subjected to a second mechanical defibration step which causes the crosslinked fibers to twist and curl between the defluidizing and drying steps. The same apparatuses and methods previously described for defibrating the fibers are applicable to this second mechanical defibration step. As used in this paragraph, the term "defibration" refers to any of the procedures which may be used to mechanically separate the fibers into substantially individual form, even though the fibers may already be provided in such form. "Defibration" therefore refers to the step of mechanically treating the fibers, in either individual form or in a more compacted form, wherein such mechanical treatment step a) separates the fibers into substantially individual form if they were not already in such form, and b) imparts curl and twist to the fibers upon drying.

This second defibration treatment, after the fibers have been crosslinked, is believed to increase the twisted, curled character of the pulp. This increase in the twisted, curled configuration of the fibers leads to enhanced absorbent structure resiliency and responsiveness to wetting.

The maximum level of crosslinking will be achieved when the fibers are essentially dry (having less than about 5% moisture). Due to this absence of water, the fibers are crosslinked while in a substantially unswollen, collapsed state. Consequently, they characteristically have low fluid retention values (FRV) relative to the range applicable to this invention. The FRV refers to the amount of fluid calculated on a dry fiber basis, that remains absorbed by a sample of fibers that have been soaked and then centrifuged to remove interfiber fluid. (The FRV is further defined and the Procedure For Determining FRV, is described below.) The amount of fluid that the crosslinked fibers can absorb is dependent upon their ability to swell upon saturation or, in other words, upon their interior diameter or volume upon swelling to a maximum level. This, in turn, is dependent upon the level of crosslinking. As the level of intrafiber crosslinking increases for a given fiber and process, the FRV of the fiber will decrease. Thus, the FRV value of a fiber is structurally descriptive of the physical condition of the fiber at saturation. Unless otherwise expressly indicated, FRV data described herein shall be reported in terms of the water retention value (WRV) of the fibers. Other fluids, such as salt water and synthetic urine, may also be advantageously utilized as a fluid medium for analysis. Generally, the FRV of a particular fiber crosslinked by procedures wherein curing is largely dependent upon drying, such as the present process, will be primarily dependent upon the crosslinking agent and the level of crosslinking. The WRV's of fibers crosslinked by this dry crosslinking process at crosslinking agent levels applicable to this invention are generally less than about 60, greater than about 28, preferably less than about 50, and more preferably between about 30 and about 45. Bleached SSK fibers having between about 1.5 mole % and about 6.0 mole % citric acid reacted thereon, calculated on a cellulose anhydroglucose molar basis, have been observed to have WRV's respectively ranging from about 28 to about 40. The degree of bleaching and the practice of post-crosslinking bleaching steps have been found to affect WRV. Southern softwood Kraft (SSK) fibers prepared by many of the prior art known crosslinking processes have levels of crosslinking higher than described herein, and have WRV's less than about 25. Such fibers, as previously discussed, have been observed to be exceedingly stiff and to exhibit lower absorbent capabilities than the fibers of the present invention.

In another process for making individualized, crosslinked fibers by a dry crosslinking process, cellulosic fibers are contacted with a solution containing a crosslinking agent as described above. Either before or after being contacted with the crosslinking agent, the fibers are provided in a sheet form. The fibers, while in sheeted form, are dried and caused to crosslink preferably by heating the fibers to a temperature of between about 120° C. and about 160° C. Subsequent to crosslinking, the fibers are mechanically separated into substantially individual form. This is preferably performed by treatment with a fiber fluffing apparatus such as the one described in U.S. Pat. No. 3,987,968 or may be performed with other methods for defibrating fibers as may be known in the art. The individualized, crosslinked fibers made according to this sheet crosslinking process are treated with a sufficient amount of crosslinking agent such that an effective amount of crosslinking agent, preferably between about 0.5 mole % and about 10.0 mole % crosslinking agent, calculated on a cellulose anhydroglucose molar basis and measured subsequent to defibration, are reacted with the fibers in the form of intrafiber crosslink bonds. Another effect of drying and crosslinking the fibers while in sheet form is that fiber to fiber bonding restrains the fibers from twisting and curling with increased drying. Compared to individualized, crosslinked fibers made according to a process wherein the fibers are dried under substantially unrestrained conditions and subsequently crosslinked in a twisted, curled configuration, absorbent structures containing the relatively untwisted fibers made by the sheet curing process described above would be expected to exhibit lower wet resiliency and lower responsiveness to wetting.

It is also contemplated to mechanically separate the fibers into substantially individual form between the drying and the crosslinking step. That is, the fibers are contacted with the crosslinking agent and subsequently dried while in sheet form. Prior to crosslinking, the fibers are individualized to facilitate intrafiber crosslinking. This alternative crosslinking method, as well as other variations which will be apparent to those skilled in the art, are intended to be within the scope of this invention.

Another category of crosslinking processes applicable to the present invention is nonaqueous solution cure crosslinking processes. The same types of fibers applicable to dry crosslinking processes may be used in the production of nonaqueous solution crosslinked fibers. The fibers are treated with a sufficient amount of crosslinking agent such that an effective amount of crosslinking agent subsequently reacts with the fibers, and with an appropriate catalyst, if desired. The amounts of crosslinking agent and catalyst (if one is used) utilized will depend upon such reaction conditions as consistency, temperature, water content in the crosslinking solution and fibers, type of crosslinking agent and diluent in the crosslinking solution, and the amount of crosslinking desired. The crosslinking agent is caused to react while the fibers are submerged in a substantially nonaqueous solution. The nonaqueous crosslinking solution contains a nonaqueous, water-miscible, polar diluent such as, but not limited to acetic acid, propanoic acid, or acetone. The crosslinking solution may also contain a limited amount of water or other fiber swelling liquid, however, the amount of water is preferably insufficient to induce any substantial levels of fiber swelling. Crosslinking solution systems applicable for use as a crosslinking medium include those disclosed in U.S. Pat. No. 4,035,147, issued to S. Sangenis, G. Guiroy, and J. Quere, on Jul. 12, 1977, which is hereby incorporated by reference into this disclosure.

The crosslinked fibers used in the absorbent structures of the present invention are preferably prepared by the dry crosslinking process discussed above. The crosslinked fibers may be utilized directly in the manufacture of air laid absorbent cores. Additionally, due to their stiffened and resilient character, the crosslinked fibers may be wet laid into an uncompacted, low density sheet which, when subsequently dried, is directly useful without further mechanical processing as an absorbent core. The crosslinked fibers may also be wet laid as compacted pulp sheets for sale or transport to distant locations.

Relative to pulp sheets made from conventional, uncrosslinked cellulosic fibers, the pulp sheets made from the crosslinked fibers of the present invention are more difficult to compress to conventional pulp sheet densities. Therefore, it may be desirable to combine crosslinked fibers with uncrosslinked fibers, such as those conventionally used in the manufacture of absorbent cores. Pulp sheets containing stiffened, crosslinked fibers preferably contain between about 5% and about 90% uncrosslinked, cellulosic fibers, based upon the total dry weight of the sheet, mixed with the individualized, crosslinked fibers. It is especially preferred to include between about 5% and about 30% of highly refined, uncrosslinked cellulosic fibers, based upon the total dry weight of the sheet. Such highly refined fibers are refined or beaten to a freeness level less than about 300 ml CSF, and preferably less than 100 ml CSF. The uncrosslinked fibers are preferably mixed with an aqueous slurry of the individualized, crosslinked fibers. This mixture may then be formed into a densified pulp sheet for subsequent defibration and formation into absorbent pads. The incorporation of the uncrosslinked fibers eases compression of the pulp sheet into a densified form, while imparting a surprisingly small loss in absorbency to the subsequently formed absorbent pads. The uncrosslinked fibers additionally increase the tensile strength of the pulp sheet and to absorbent pads made either from the pulp sheet or directly from the mixture of crosslinked and uncrosslinked fibers. Regardless of whether the blend of crosslinked and uncrosslinked fibers are first made into a pulp sheet and then formed into an absorbent pad or formed directly into an absorbent pad, the absorbent pad may be air-laid or wet-laid.

Sheets or webs made from the individualized, crosslinked fibers, or from mixtures also containing uncrosslinked fibers, will preferably have basis weights of less than about 800 $g/m^2$ and densities of less than about 0.60 $g/cm^3$. Although it is not intended to limit the scope of the invention, wet-laid sheets having basis weights between 300 $g/m^2$ and about about 600 $g/m^2$ and densities between 0.07 $g/cm^3$ and about 0.30 $g/cm^3$ are especially contemplated for direct application as absorbent cores in disposable articles such as diapers, tampons, and other catamenial products. Structures having basis weights and densities higher than these levels are believed to be most useful for subsequent comminution and air-laying or wet-laying to form a lower density and basis weight structure which is more useful for absorbent applications. Although, such higher basis weight and density structures also exhibit surprisingly high absorptivity and responsiveness to wetting. Other applications contemplated for the fibers of the present invention include low density tissue sheets having densities which may be less than about 0.03 g/cc.

If desired, the crosslinked fibers can be further processed to remove excess, unreacted crosslinking agent. One series of treatments found to successfully remove excess crosslinking agent comprise, in sequence, washing the crosslinked fibers, allowing the fibers to soak in an aqueous solution for an appreciable time, screening the fibers, dewatering the fibers, e.g., by centrifuging, to a consistency of between about 40% and about 80%, mechanically defibrating the dewatered fibers as previously described and air drying the fibers. A sufficient amount of an acidic substance may be added to the wash solution, if necessary, to keep the wash solution at a pH of less than about 7. Without being bound by theory, it is believed that the ester crosslinks are not stable under alkaline conditions and that keeping the wash treatment pH in the acidic range inhibits reversion of the ester crosslinks which have formed. Acidity may be introduced by mineral acids such as sulfuric acid, or alternatively in the form of acidic bleach chemicals such as chlorine dioxide and sodium hydrosulfite (which may also be added to brighten the crosslinked fibers). This process has been found to reduce residual free crosslinking agent content to between about 0.01% and about 0.15%.

The crosslinked fibers herein described are useful for a variety of absorbent articles including, but not limited to, tissue sheets, disposable diapers, catamenials, sanitary napkins, tampons, and bandages wherein each of said articles has an absorbent structure containing the individualized, crosslinked fibers described herein. For example, a disposable diaper or similar article having a liquid permeable topsheet, a liquid impermeable backsheet connected to the topsheet, and an absorbent structure containing individualized, crosslinked fibers is particularly contemplated. Such articles are described generally in U.S. Pat. No. 3,860,003, issued to Kenneth B. Buell on Jan. 14, 1975, hereby incorporated by reference into this disclosure.

Conventionally, absorbent cores for diapers and catamenials are made from unstiffened, uncrosslinked cellulosic fibers, wherein the absorbent cores have dry densities of about 0.06 g/cc and about 0.12 g/cc. Upon wetting, the absorbent core normally displays a reduction in volume.

It has been found that the crosslinked fibers of the present invention can be used to make absorbent cores having substantially higher fluid absorbing properties including, but not limited to, absorbent capacity and wicking rate relative to equivalent density absorbent cores made from conventional, uncrosslinked fibers or prior known crosslinked fibers. Furthermore, these improved absorbency results may be obtained in conjunction with increased levels of wet resiliency. For absorbent cores having densities of between about 0.05 g/cc and about 0.15 g/cc which maintain substantially constant volume upon wetting, it is especially preferred to utilize crosslinked fibers having crosslinking levels of between about 5.0 mole % and about 10.0 mole % crosslinking agent, based upon a dry cellulose anhydroglucose molar basis. Absorbent cores made from such fibers have a desirable combination of structural integrity, i.e., resistance to compression, and wet resilience. The term wet resilience, in the present context, refers to the ability of a moistened pad to spring back towards its original shape and volume upon exposure to and release from compressional forces. Compared to cores made from untreated fibers, and prior known crosslinked fibers, the absorbent cores made from the fibers of the present invention will regain a substantially higher proportion of their original volumes upon release of wet compressional forces.

In another preferred embodiment, the individualized, crosslinked fibers are formed into either an air laid or wet laid (and subsequently dried) absorbent core which is compressed to a dry density less than the equilibrium wet density of the pad. The equilibrium wet density is the density of the pad, calculated on a dry fiber basis when the pad is fully saturated with fluid. When fibers are formed into an absorbent core having a dry density less than the equilibrium wet density, upon wetting to saturation, the core will collapse to the equilibrium wet density. Alternatively, when fibers are formed into an absorbent core having a dry density greater than the equilibrium wet density, upon wetting to saturation, the core will expand to the equilibrium wet density. Pads made from the fibers of the present invention have equilibrium wet densities which are substantially lower than pads made from conventional fluffed fibers. The fibers of the present invention can be compressed to a density higher than the equilibrium wet density, to form a thin pad which, upon wetting, will expand, thereby increasing absorbent capacity, to a degree significantly greater than obtained for uncrosslinked fibers.

In another preferred embodiment, high absorbency properties, wet resilience, and responsiveness to wetting may be obtained for crosslinking levels of between about 1.5 mole % and about 6.0 mole %, calculated on a dry cellulose molar basis. Preferably, such fibers are formed into absorbent cores having dry densities greater than their equilibrium wet densities. Preferably, the absorbent cores are compressed to densities of between about 0.12 g/cc and about 0.60 g/cc, wherein the corresponding equilibrium wet density is less than the density of the dry compressed pad. Also, preferably the absorbent cores are compressed to a density of between about 0.12 g/cc and about 0.40 g/cc, wherein the corresponding equilibrium wet densities are between about 0.08 g/cc and about 0.12 g/cc, and are less than the densities of the dry, compressed cores. It should be recognized, however, that absorbent structures within the higher density range can be made from crosslinked fibers having higher crosslinking levels, as can lower density absorbent structures be made from crosslinked fibers having lower levels of crosslinking. Improved performance relative to prior known individualized, crosslinked fibers is obtained for all such structures.

While the foregoing discussion involves preferred embodiments for high and low density absorbent structures, it should be recognized that a variety of combinations of absorbent structure densities and crosslinking agent levels between the ranges disclosed herein will provide superior absorbency characteristics and absorbent structure integrity relative to conventional cellulosic fibers and prior known crosslinked fibers. Such embodiments are meant to be included within the scope of this invention.

Absorbent structures made from individualized, crosslinked fibers may additionally contain discrete particles of substantially water-insoluble, hydrogel-forming material. Hydrogel-forming materials are chemical compounds capable of absorbing fluids and retaining them under moderate pressures.

Suitable hydrogel-forming materials can be inorganic materials such as silica gels or organic compounds such as crosslinked polymers. It should be understood that crosslinking, when referred to in connection with hydrogel-forming materials, assumes a broader meaning than contemplated in connection with the reaction of crosslinking agents with cellulosic fibers to form individualized, crosslinked fibers. Crosslinked hydrogel-forming polymers may be crosslinked by covalent, ionic, Van der Waals, or hydrogen bonding. Examples of hydrogel-forming materials include polyacrylamides, polyvinyl alcohol, ethylene maleic anhydride copolymers, polyvinyl ethers, hydroxypropyl cellulose, carboxymethyl cellulose, polyvinyl morpholinone, polymers and copolymers of vinyl sulfonic acid, polyacrylates, polyacrylamides, polyvinyl pyridine and the like. Other suitable hydrogel-forming materials are those disclosed in Assarsson et al., U.S. Pat. No. 3,901,236, issued Aug. 26, 1975, the disclosure of which is incorporated herein by reference. Particularly preferred hydrogel-forming polymers for use in the absorbent core are hydrolyzed acrylonitrile grafted starch, acrylic acid grafted starch, polyacrylates, and isobutylene maleic anhydride copolymers, or mixtures thereof. Examples of hydrogel-forming materials which may be used are Aqualic L-73, a partially neutralized polyacrylic acid made by Nippon Shokubai Co., Japan, and Sanwet IM 1000, a partially neutralized acrylic acid grafted starch made by Sanyo Co., Ltd., Japan. Hydrogel forming materials having relatively high gel strengths, as described in U.S. Pat. No. 4,654,039, issued Mar. 31, 1987, hereby incorporated herein by reference, are preferred for utilization with individualized, crosslinked fibers.

Process for preparing hydrogel-forming materials are disclosed in Masuda et al., U.S. Pat. No. 4,076,663, issued Feb. 28, 1978; in Tsubakimoto et al., U.S. Pat. No. 4,286,082, issued Aug. 25, 1981; and further in U.S. Pat. Nos. 3,734,876, 3,661,815, 3,670,731, 3,664,343, 3,783,871, and Belgian Patent 785,850, the disclosures of which are all incorporated herein by reference.

The hydrogel-forming material may be distributed throughout an absorbent structure containing individualized, crosslinked fibers, or be limited to distribution throughout a particular layer or section of the absorbent structure. In another embodiment, the hydrogel-forming material is adhered or laminated onto a sheet or film which is juxtaposed against a fibrous, absorbent structure, which may include individualized, crosslinked fibers. Such sheet or film may be multilayered such that the hydrogel-forming material is contained between the layers. In another embodiment, the hydrogel-forming material may be adhered directly onto the surface fibers of the absorbent structure.

Surprisingly large increases in skin dryness have been observed for absorbent structures combining the individualized, crosslinked fibers of the present invention and hydrogel-forming materials, according to the skin wetness level measured by an evaporimeter subsequent to contacting moistened absorbent structures to human skin. This improvement is believed due to the high wicking ability of individualized, crosslinked fibers relative to conventional fibers and the increased absorptive capacity of the structure. Unique wicking ability of structures made from individualized, crosslinked fibers results from the stiff nature of the fibers and the relatively large void spaces resulting therefrom. However, excessively high levels of crosslinking agent, as may be present in certain prior known individualized, crosslinked fibers, may reduce wicking due to the hydrophobic characteristics of the crosslinking agent.

Another important advantage has been observed with respect to absorbent structures made from individualized, crosslinked fibers having dry densities which are higher than their corresponding equilibrium wet densities (calculated on a dry fiber basis). Specifically, this type of absorbent structure expands in volume upon wetting. As a result of this expansion, the interfiber capillary network of fibers also enlarges. In conventional absorbent structures having hydrogel-forming material blended therein, the hydrogel-forming material expands in volume due to fluid absorption, and may block or reduce in size the capillary routes for fluid absorption prior to utilization of the entire fluid absorbing potential of the structure. This phenomenon is known as gel blocking. Capillary enlargement due to expansion of fibrous network of the absorbent structure reduces the occurrence of gel blocking. This allows larger proportions of the fluid absorbency potential of the structure to be utilized and allows higher levels of hydrogel-forming material (if desired) to be incorporated into the absorbent structure, without significant levels of gel-blocking.

Absorbent structures containing individualized, crosslinked fibers and hydrogel-forming material for diaper core applications preferably have dry densities of between about 0.15 g/cc and about 0.40 g/cc and preferably contain less than about 20% hydrogel-forming material, calculated on a dry fiber weight basis. Most preferably, the individualized, crosslinked fibers have between about 1.5 mole % and about 6.0 mole % citric acid, calculated on a cellulose anhydroglucose molar basis, reacted therewith in the form of intrafiber crosslink bonds wherein the fibers are formed into a relatively thin absorbent structure in a sufficiently compressed dry state such that the structure may expand upon wetting.

The hydrogel-forming material may be homogeneously dispersed throughout all or part of the absorbent structure. For a diaper structure as disclosed in U.S. Pat. No. 3,860,003 having an absorbent core which contains the preferred individualized, crosslinked fibers, has a dry density of about 0.20 g/cc, and also contains hydrogel-forming material dispersed throughout the core. It is presently believed that an optimal balance of diaper wicking, total absorbent capacity, skin wetness, and economic viability is obtained for contents of between about 5 wt. % and about 20 wt. %, based on the total weight of the dry absorbent core, of a hydrogen forming material such as Aqualic L-73. Between about 8 wt. % and about 10 wt. % of hydrogel-forming material is preferably homogeneously blended with the individualized, crosslinked fiber-containing absorbent cores in products as disclosed in U.S. Pat. No. 3,860,003.

The absorbent structures described above may also include conventional, fluffed fibers, or highly refined fibers, wherein the amount of hydrogel-forming material is based upon the total weight of the fibers as previously discussed. The embodiments disclosed herein are exemplary in nature and are not meant to limit the scope of application of hydrogel-forming materials with individualized, crosslinked fibers.

PROCEDURE FOR DETERMINING FLUID RETENTION VALUE

The following procedure can be utilized to determine the water retention value of cellulosic fibers.

A sample of about 0.3 g to about 0.4 g of fibers is soaked in a covered container with about 100 ml distilled or deionized water at room temperature for between about 15 and about 20 hours. The soaked fibers are collected on a filter and transferred to an 80-mesh wire basket supported about 1½ inches above a 60-mesh screened bottom of a centrifuge tube. The tube is covered with a plastic cover and the sample is centrifuged at a relative centrifuge force of 1500 to 1700 gravities for 19 to 21 minutes. The centrifuged fibers are then removed from the basket and weighed. The weighed fibers are dried to a constant weight at 105° C. and reweighed. The water retention value is calculated as follows:

$$WRV = \frac{(W - D)}{D} \times 100 \tag{1}$$

where,
W = wet weight of the centrifuged fibers;
D = dry weight of the fibers; and
W-D = weight of absorbed water.

PROCEDURE FOR DETERMINING DRIP CAPACITY

The following procedure can be utilized to determine drip capacity of absorbent cores. Drip capacity is utilized as a combined measure of absorbent capacity and absorbency rate of the cores.

A four inch by four inch absorbent pad weighing about 7.5 g is placed on a screen mesh. Synthetic urine is applied to the center of the pad at a rate of 8 ml/s. The flow of synthetic urine is halted when the first drop of synthetic urine escapes from the bottom or sides of the pad. The drip capacity is calculated by the difference in mass of the pad prior to and subsequent to introduction of the synthetic urine divided by the mass of the fibers, bone dry basis.

PROCEDURE FOR DETERMINING WET COMPRESSIBILITY

The following procedure can be utilized to determine wet compressibility of absorbent structures. Wet compressibility is utilized as a measure of resistance to wet compression, wet structural integrity and wet resilience of the absorbent cores.

A four inch by four inch square pad weighing about 7.5 g is prepared, its thickness measured and density calculated. The pad is loaded with synthetic urine to ten times its dry weight or to its saturation point, whichever is less. A 0.1 PSI compressional load is applied to the pad. After about 60 seconds, during which time the pad equilibrates, the thickness of the pad is measured. The compressional load is then increased to 1.1 PSI, the pad is allowed to equilibrate, and the thickness is measured. The compressional load is then reduced to 0.1 PSI, the pad allowed to equilibrate and the thickness is again measured. The densities are calculated for the pad at the original 0.1 PSI load, the 1.1 PSI load and the second 0.1 PSI load, referred to as 0.1 PSIR (PSI rebound) load. The void volume reported in cc/g, is then determined for each respective pressure load. The void volume is the reciprocal of the wet pad density minus the fiber volume (0.95 cc/g). The 0.1 PSI and 1.1 PSI void volumes are useful indicators of resistance to wet compression and wet structural integrity. Higher void volumes for a common initial pad densities indicate greater resistance to wet compression and greater wet structural integrity. The difference between 0.1 PSI and 0.1 PSIR void volumes is useful for comparing wet resilience of absorbent pads. A smaller difference between 0.1 PSI void volume and 0.1 PSIR void volume, indicates higher wet resilience.

Also, the difference in caliper between the dry pad and the saturated pad prior to compression is found to be a useful indicator of the responsiveness to wetting of the pads.

PROCEDURE FOR DETERMINING DRY COMPRESSIBILITY

The following procedure can be utilized to determine dry compressibility of absorbent cores. Dry compressibility is utilized as a measure of dry resilience of the cores.

A four inch by four inch square air laid pad having a mass of about 7.5 g is prepared and compressed, in a dry state, by a hydraulic press to a pressure of 5500 lbs/16 in$^2$. The pad is inverted and the pressing is repeated. The thickness of the pad is measured before and after pressing with a no-load caliper. Density before and after pressing is then calculated as mass/(area X thickness). Larger differences between density before and after pressing indicate lower dry resilience.

PROCEDURE FOR DETERMINING LEVEL OF $C_2$–$C_9$ POLYCARBOXYLIC ACID REACTED WITH CELLULOSIC FIBERS

There exist a variety of analytical methods suitable for determining the level of polycarboxylic acid crosslinked with cellulosic fibers. Any suitable method can be used. For the purposes of determining the level of preferred $C_2$–$C_9$ polycarboxylic acid (e.g., citric acid, 1,2,3 propane tricarboxylic acid, 1,2,3,4 butane tetracarboxylic acid and oxydisuccinic acid) which reacts to form intrafiber crosslink bonds with the cellulosic component of the individualized, crosslinked fibers in the examples of the present invention, the following procedure is used. First, a sample of the crosslinked fibers is washed with sufficient hot water to remove any unreacted crosslinking chemicals or catalysts. Next, the fibers are dried to equilibrium moisture content. The carboxyl group content of the individualized, crosslinked fibers is then determined essentially in accordance with T.A.P.P.I. Method T 237 OS-77. The crosslinking level of the $C_2$–$C_9$ polycarboxylic acid is then calculated from the fiber's carboxyl group content by the following formula:

$$\text{Crosslinking level (Mole \%)} = (C-30)\left(\frac{1 \text{ kg pulp}}{1000 \text{ g pulp}}\right)\left(\frac{162 \text{ g pulp}}{1 \text{ mole pulp}^*}\right)\left(\frac{0.001 \text{ eq.}}{\text{meq.}}\right)\left(\frac{1 \text{ mole carboxylic acid}}{1 \text{ eq. free carboxyl group}}\right)$$

Where C=carboxyl content of crosslinked fibers, meq/kg
30=carboxyl content of uncrosslinked pulp fibers meq/kg
*162 g/mole=molecular weight of crosslinked pulp fibers (i.e., one anhydroglucose unit)

The assumptions made in deriving the above formula are:

1. The molecular weight of the crosslinked fibers is equivalent to that of uncrosslinked pulp, i.e., 162 g/mole (calculated on an cellulose anhydroglucose molar basis). 2. Two of citric acid's three carboxyl groups react with hydroxyl groups on the cellulose to form a crosslink bond, thus leaving one carboxyl group free to be measured by the carboxyl test.

3. Two of tricarballylic acid's (TCBA, also known as 1,2,3 propane tricarboxylic acid) three carboxyl groups react with two hydroxyl groups on the cellulose to form a crosslink bond, thus leaving one carboxyl group free to be measured by the carboxyl test.

4. Three of 1,2,3,4 butane tetracarboxylic acid's (BTCA) four carboxyl groups react with hydroxyl groups on the cellulose to form a crosslink bond, thus leaving one carboxyl group free to be measured by the carboxyl test.

5. Three of oxydisuccinic acid's (ODS) four carboxyl groups react with hydroxyl groups on the cellulose to form crosslink bond, thus leaving one carboxyl group free to be measured by the carboxyl test.

6. Uncrosslinked pulp fibers have a carboxyl content of 30 meq/kg.

7. No new carboxyl groups are generated on the cellulose during the crosslinking process.

PROCEDURE FOR DETERMINING TWIST COUNT

The following method can be used to determine the twist count of fibers analyzed in this disclosure.

Dry fibers are placed on a slide coated with a thin film of immersion oil, and then covered with a cover slip. The effect of the immersion oil was to render the fiber transparent without inducing swelling and thereby aid in identification of the twist nodes (described below). Wet fibers are placed on a slide by pouring a low consistency slurry of the fibers on the slide which is then covered with a cover slip. The water rendered the fibers transparent so that twist node identification is facilitated.

An image analyzer comprising a computer-controlled microscope, a video camera, a video screen, and a computer loaded with QUIPS software, available from Cambridge Instruments Limited (Cambridge, England; Buffalo, NY), is used to determine twist count.

The total length of fibers within a particular area of the microscope slide at 200X magnification is measured by the image analyzer. The twist nodes are identified and marked by an operator. This procedure is continued, measuring fiber length and marking twist nodes until 1270 mm inches of total fiber length are analyzed. The number of twist nodes per millimeter is calculated from this data by dividing the total fiber length into the total number of twist nodes marked.

PROCEDURE FOR DETERMINING CURL FACTOR

The following method can be utilized to measure fiber curl index.

Dry fibers are placed onto a microscope slide. A cover slip is placed over the fibers and glued in place at the edges. The actual length $L_A$ and the maximum projected length $L_R$ (equivalent to the length of the longest side of a rectangle encompassing the fiber) are measured utilizing an image analyzer comprising a software controlled microscope, video camera, video monitor, and computer. The software utilized is the same as that described in the Twist Count Image Analysis Method section above.

Once $L_A$ and $L_R$ are obtained, the curl factor is calculated according to Equation (1) shown above. The curl factor for each sample of fiber is calculated for at least 250 individual fibers and then averaged to determine the mean curl factor for the sample. Fibers having $L_A$ less than 0.25 mm are excluded from the calculation.

The following examples illustrate the practice of the present invention but are not intended to be limiting thereof.

EXAMPLE I

Individualized, crosslinked fibers used in the absorbent structures of the present invention are made by a dry crosslinking process utilizing citric acid as the crosslinking agent. The procedure used to produce the citric acid crosslinked fibers is as follows:

1. For each sample, 1,735 g of once dried, southern softwood kraft (SSK) pulp is provided. The fibers have a moisture content of about 7% (equivalent to 93% consistency).

2. A slurry is formed by adding fibers to an aqueous solution containing about 2,942 g of citric acid and 410 ml of 50% sodium hydroxide solution in 59,323 g of H$_2$O. The fibers are soaked in the slurry for about 60 minutes. This step is also referred to as "steeping". The steep pH is about 3.0.

3. The fibers are then dewatered by centrifuging to a consistency ranging from about 40% to about 50%. the centrifuged slurry consistency of this step combined with the carboxylic acid concentration in the slurry filtrate in step 2 set the amount of crosslinking agent present on the fibers after centrifuging. In this example, about 6 weight % of citric acid, on a dry fiber cellulose anhydroglucose basis is present on the fibers after the initial centrifuging. In practice, the concentration of the crosslinking agent in the slurry filtrate is calculated by assuming a targeted dewatering consistency and a desired level of chemicals on the fibers.

4. Next, the dewatered fibers are defibrated using a Sprout-Waldron 12" disk refiner (model number 105-A) whose plates are set at a gap which yields fibers substantially individualized but with a minimum amount of fiber damage. As the individualized fibers exit the refiner, they are flash dried with hot air in two vertical tubes in order to provide fiber twist and curl. The fibers contain approximately 10% moisture upon exiting these tubes and are ready to be cured. If the moisture content of the fibers is greater than about 10% upon exiting the flash drying tubes, then the fibers are dried with ambient temperature air until the moisture content is about 10%.

5. The nearly dry fibers are then placed on trays and cured in an air-through drying oven for a length of time and at a temperature which in practice depends on the amount of citric acid added, dryness of the fibers, etc. In this example, the samples are cured at a temperature of about 188° C. for a period of about 8 minutes. Crosslinking is completed during the period in the oven.

6. The crosslinked, individualized fibers are placed on a mesh screen and rinsed with about 20° C. water, soaked at 1% consistency for one (1) hour in about 60° C. water, screened, rinsed with about 20° C. water for a second time, centrifuged to about 60% fiber consistency, and dried to an equilibrium moisture content of about 8% with ambient temperature air.

The resulting individualized crosslinked cellulosic fibers have a WRV of 37.6 and contain 3.8 mole % citric acid, calculated on a cellulose anhydroglucose molar basis, reacted with the fibers in the form of intrafiber crosslink bonds.

The dried fibers are air laid to form absorbent pads. The pads are compressed with a hydraulic press to a density of 0.20 g/cc. The pads are tested for absorbency, resiliency, and amount of citric acid reacted according to the procedures defined herein. Citric acid reacted is reported in mole % calculated on a dry fiber cellulose anhydroglucose basis. The results are reported in Table 1 and are compared to an absorbent pad made from conventional, uncrosslinked cellulosic fibers.

TABLE 1

| Sample # | Citric Acid (mole %) Reacted | WRV (%) | Drip Cap. @ 8 ml/s (g/g) | Wet Compressibility (cc/g) | | |
|---|---|---|---|---|---|---|
| | | | | 0.1 PSI | 1.1 PSI | 0.1 PSIR |
| 1 | 0 | 79.2 | 4.56 | 8.95 | 5.38 | 5.90 |
| 2 | 3.8 | 37.6 | 14.55 | 10.29 | 6.68 | 7.38 |

As can be seen from Table 1, the absorbent pads containing individualized, citric acid crosslinked fibers (i.e., Sample 2) have significantly higher drip capacities and wet compressibilities at 0.1 PSI, 1.1 PSI and 0.1 PSIR relative to pads containing conventional, uncrosslinked fibers (i.e., Sample 1). In addition to having improved responsiveness to wetting relative to conventional uncrosslinked fibers, the absorbent pads containing citric acid crosslinked fibers can be safely utilized in the vicinity of human skin.

EXAMPLE II

The individualized, crosslinked fibers of Example I are air laid to form absorbent pads, and compressed with a hydraulic press to a density of 0.10 g/cc. The pads are subsequently tested for absorbency, resiliency, and structural integrity according to the previously outlined wet compressibility procedure. The results are reported in Table 2.

TABLE 2

| Sample # | Wet Compressibility (cc/g) | | |
|---|---|---|---|
| | 0.1 PSI | 1.1 PSI | 0.1 PSIR |
| 1 | 10.68 | 6.04 | 6.46 |
| 2 | 11.87 | 7.67 | 8.48 |

As can be seen from Table 2, the absorbent pads—at a dry fiber density of 0.10 g/cc—containing individualized, citric acid crosslinked fibers (i.e., Sample 2) have significantly higher wet compressibilities at 0.1 PSI, 1.1 PSI, and 0.1 PSIR relative to pads containing conventional, uncrosslinked fibers (i.e., Sample 1). In addition to having improved responsiveness to wetting, the absorbent pads containing citric acid crosslinked fibers can be safely utilized in the vicinity of human skin.

EXAMPLE III

Individualized crosslinked fibers used in the absorbent structures of the present invention are made by a dry crosslinking process utilizing 1,2,3,4 butane tetracarboxylic acid (BTCA) as the crosslinking agent. The individualized crosslinked fibers are produced in accordance with the hereinbefore described process of Example I with the following modifications: The slurry in step 2 of Example I contains 150 g of dry pulp, 1186 g of $H_2O$, 64 g of BTCA and 4 g of sodium hydroxide. In step 5, the fibers are cured at a temperature of about 165° C. for a period of about 60 minutes.

The resulting individualized crosslinked cellulosic fibers have a WRV of 32.9 and contain 5.2 mole % 1,2,3,4 butane tetracarboxylic acid, calculated on a cellulose anhydroglucose molar basis, reacted with the fibers in the form of intrafiber crosslink bonds.

The dried fibers are air laid to form absorbent pads. The pads are compressed with a hydraulic press to a density of 0.20 g/cc. The pads are tested for absorbency, resiliency, and amount of 1,2,3,4 butane tetracarboxylic acid (BTCA) reacted according to the procedures defined herein. BTCA reacted is reported in mole % calculated on a dry fiber cellulose anhydroglucose basis. The results are reported in Table 3 and are compared to an absorbent pad made from conventional, uncrosslinked cellulosic fibers.

TABLE 3

| Sample # | BTCA (mole %) Reacted | WRV (%) | Drip Cap. @ 8 ml/s (g/g) | Wet Compressibility (cc/g) | | |
|---|---|---|---|---|---|---|
| | | | | 0.1 PSI | 1.1 PSI | 0.1 PSIR |
| 1 | 0 | 79.2 | 4.56 | 8.95 | 5.38 | 5.90 |
| 3 | 5.2 | 32.9 | 13.43 | 9.58 | 6.30 | 7.05 |

As can be seen from Table 3, the absorbent pads containing individualized, BTCA crosslinked fibers (i.e., Sample 3) have significantly higher drip capacities and wet compressibilities at 0.1 PSI, 1.1 PSI, and 0.1 PSIR relative to pads containing conventional, uncrosslinked fibers (i.e., Sample 1). In addition to having improved responsiveness to wetting, the absorbent pads containing BTCA crosslinked fibers can be safely utilized in the vicinity of human skin.

EXAMPLE IV

The individualized, crosslinked fibers of Example III are air laid into absorbent pads, and compressed with a hydraulic press to a density of 0.10 g/cc. The pads are subsequently tested for absorbency, resiliency, and structural integrity according to the previously outlined wet compressibility procedure. The results are reported in Table 4.

TABLE 4

| Sample # | Wet Compressibility (cc/g) | | |
|---|---|---|---|
| | 0.1 PSI | 1.1 PSI | 0.1 PSIR |
| 1 | 10.68 | 6.04 | 6.46 |
| 3 | 11.71 | 7.52 | 8.53 |

As can be seen from Table 4, the absorbent pads—at a dry fiber density of 0.10 g/cc—containing individualized, BTCA crosslinked fibers (i.e., Sample 3) have significantly higher wet compressibilities at 0.1 PSI, 1.1 PSI, and 0.1 PSIR relative to pads at the same density containing conventional, uncrosslinked fibers (i.e., Sample 1). In addition to having improved responsiveness to wetting, the absorbent pads containing BTCA crosslinked fibers can be safely utilized in the vicinity of human skin.

In Examples III and IV, substantially similar results are obtained when the 1,2,3,4 butane tetracarboxylic acid (BTCA) crosslinking agent is replaced in whole, or in part, by an equivalent amount of 1,2,3 propane tricarboxylic acid.

EXAMPLE V

Individualized crosslinked fibers used in the absorbent structures of the present invention are made by a dry crosslinking process utilizing oxydisuccinic acid (ODS) as the crosslinking agent. The individualized crosslinked fibers are produced in accordance with the hereinbefore described process of Example I with the following modifications: The slurry in step 2 of Example I contains 140 g of dry pulp, 985 g of $H_2O$, 40 g of sodium salt of ODS and 10 ml of 98% sulfuric acid.

The resulting individualized crosslinked cellulosic fibers have a WRV of 44.3 and contain 3.6 mole % oxydisuccinic acid, calculated on a cellulose anhydroglucose molar basis, reacted with the fibers in the form of intrafiber crosslink bonds.

The dried fibers are air laid to form absorbent pads. The pads are compressed with a hydraulic press to a density of 0.20 g/cc. The pads are tested for absorbency, resiliency, and amount of oxydisuccinic acid (ODS) reacted according to the procedures defined herein. ODS reacted is reported in mole % calculated on a dry fiber cellulose anhydroglucose basis. The results are reported in Table 5 and are compared to an absorbent pad made from conventional, uncrosslinked cellulosic fibers.

TABLE 5

| Sample # | ODS (mole %) Reacted | WRV (%) | Drip Cap. @ 8 ml/s (g/g) | Wet Compressibility (cc/g) | | |
|---|---|---|---|---|---|---|
| | | | | 0.1 PSI | 1.1 PSI | 0.1 PSIR |
| 1 | 0 | 79.2 | 4.56 | 8.95 | 5.38 | 5.90 |
| 4 | 3.6 | 44.3 | 14.3 | 10.04 | 6.24 | 6.86 |

As can be seen from Table 4, the absorbent pads containing individualized, ODS crosslinked fibers (i.e., Sample 4) have significantly higher drip capacities and wet compressibilities at 0.1 PSI, 1.1 PSI, and 0.1 PSIR relative to pads containing conventional, uncrosslinked fibers (i.e., Sample 1). In addition to having improved responsiveness to wetting, the absorbent pads containing ODS crosslinked fibers can be safely utilized in the vicinity of human skin.

EXAMPLE VI

The individualized, crosslinked fibers of Example V are air laid into absorbent pads, and compressed with a hydraulic press to a density of 0.10 g/cc. The pads are subsequently tested for absorbency, resiliency, and structural integrity according to the previously outlined wet compressibility procedure. The results are reported in Table 6.

TABLE 6

| Sample # | Wet Compressibility (cc/g) | | |
|---|---|---|---|
| | 0.1 PSI | 1.1 PSI | 0.1 PSIR |
| 1 | 10.68 | 6.04 | 6.46 |
| 4 | 11.25 | 7.25 | 7.90 |

As can be seen from Table 6, the absorbent pads—at a dry fiber density of 0.10 g/cc—containing individualized, crosslinked fibers (i.e., Sample 4) have significantly higher wet compressibilities at 0.1 PSI, 1.1 PSI, and 0.1 PSIR relative to pads at the same density containing conventional, uncrosslinked fibers (i.e., Sample 1). In addition to having improved responsiveness to wetting, the absorbent pads containing ODS crosslinked fibers can be safely utilized in the vicinity of human skin.

What is claimed is:

1. An absorbent structure comprising individualized, crosslinked wood pulp cellulosic fibers having between about 0.5 mole % and about 10.0 mole % of a $C_2$-$C_9$ polycarboxylic acid crosslinking agent, calculated on a cellulose anhydroglucose molar basis, reacted with said fibers in an intrafiber ester crosslink bond form, wherein said crosslinked fibers have a water retention value of from about 25 to about 60, and wherein said $C_2$-$C_9$ polycarboxylic acid crosslinking agent is selected from the group consisting of:
   (i) aliphatic and alicyclic $C_2$-$C_9$ polycarboxylic acids having at least three carboxyl groups per molecule; and
   (ii) aliphatic and alicyclic $C_2$-$C_9$ polycarboxylic acids having two carboxyl groups per molecule and having a carbon-carbon double bond located alpha, beta to one or both of the carboxyl groups, wherein one carboxyl group in said $C_2$-$C_9$ polycarboxylic acid crosslinking agent is separated from a second carboxyl group by either two or three carbon atoms.

2. The absorbent structure of claim 1 wherein said fibers have between about 1.5 mole % and about 6.0 mole % crosslinking agent, calculated on a cellulose anhydroglucose molar basis, reacted therewith in the form of intrafiber ester crosslink bonds.

3. The absorbent structure of claim 1 wherein said crosslinking agent is selected from the group consisting of citric acid, 1, 2, 3, 4 butane tetracarboxylic acid, and 1, 2, 3 propane tricarboxylic acid.

4. The absorbent structure of claim 3 wherein said crosslinking agent is citric acid.

5. The absorbent structure of claim 2 wherein said crosslinking agent is selected from the group consisting of citric acid, 1,2,3,4 butane tetracarboxylic acid, and 1,2,3 propane tricarboxylic acid.

6. The absorbent structure of claim 5 wherein said crosslinking agent is citric acid.

7. The absorbent structure of claim 6 wherein said water retention value is between about 28 and about 50.

8. The absorbent structure of claim 1 wherein said crosslinking agent is selected from the group consisting of oxydisuccinic acid, tartrate monosuccinic acid having the formula

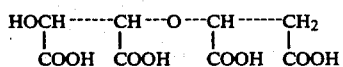

and tartrate disuccinic acid having the formula

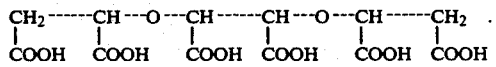

9. The absorbent structure of claim 8 wherein said crosslinking agent is oxydisuccinic acid.

10. The absorbent structure of claim 8 wherein said fibers have between about 1.5 mole % and about 6.0 mole % crosslinking agent, calculated on a cellulose anhydroglucose molar basis, reacted therewith in the form of intrafiber crosslink bonds.

11. The absorbent structure of claim 10 wherein said water retention value is between about 28 and about 50.

12. The absorbent structure of claim 1, 4, 7, or 8, having a dry density and an equilibrium wet density calculated on a dry fiber weight basis, said dry density being greater than said equilibrium wet density.

13. The absorbent structure of claim 1, 4 or 8 wherein said absorbent structure has a dry density of less than about 0.60 g/cc.

14. The absorbent structure of claim 1, 4 or 8 wherein said absorbent structure has a dry density of between about 0.05 g/cc and about 0.15 g/cc.

15. The absorbent structure of claim 7 wherein said absorbent structure has a dry fiber density of between about 0.12 g/cc and about 0.60 g/cc and an equilibrium wet density, calculated on a dry fiber basis, which is less than said actual dry fiber density.

16. The absorbent structure of claim 11 wherein said absorbent structure has a dry fiber density of between about 0.12 g/cc and about 0.60 g/cc and an equilibrium wet density, calculated on a dry fiber basis, which is less than said actual dry fiber density.

17. The absorbent structure of claim 1 wherein said structure comprises between about 70% and about 95% individualized crosslinked fibers, and between about 30% and about 5% uncrosslinked cellulosic fibers.

18. The absorbent structure of claim 1 further comprising a hydrogel-forming material disposed upon said fibers.

19. The absorbent structure of claim 1 further comprising a hydrogel-forming material disposed within said absorbent structure.

20. The absorbent structure of claim 19 wherein said hydrogel-forming material is substantially homogeneously blended throughout at least part of said absorbent structure.

21. The absorbent structure of claim 19 wherein said hydrogel-form material is disposed upon a sheet, said sheet being placed against said fibers.

22. The absorbent structure of claim 17 further comprising a hydrogen-forming material disposed within said absorbent structure.

23. A disposable absorbent article comprising a topsheet, a backsheet connected to said topsheet, and an absorbent structure as recited in claim 1, 15, 16, 18, 19, or 22, disposed between said topsheet and said backsheet.

24. The absorbent structure of claim 1 wherein said absorbent structure has a basis weight of less than about 800 g/m$^2$, and a dry density of less than about 0.60 g/cc.

25. The absorbent structure of claim 19 having a dry density and an equilibrium wet density, calculated on a dry fiber weight basis, said dry density being greater than said equilibrium wet density.

26. The absorbent structure of claim 25 wherein said absorbent structure has a dry density of between about 0.12 g/cc and about 0.60 g/cc.

27. The absorbent structure of claim 26 wherein said fibers have between about 1.5 mole % and about 6.0 mole % crosslinking agent, calculated on a cellulose anhydroglucose molar basis, the water retention value of said fibers is from about 28 to about 50, and wherein said crosslinking agent is citric acid.

* * * * *